United States Patent [19]

Ekimoto et al.

[11] Patent Number: 4,824,955
[45] Date of Patent: Apr. 25, 1989

[54] SELENIUM OXY CHLORIDE-PYRIDINE OR BIPYRIDINE COMPLEXES

[75] Inventors: Hisao Ekimoto, Tokyo; Masanobu Suzuki; Takao Izawa, both of Yono; Katsutoshi Takahashi, Tokyo; Tokuji Nakatani, Saitama; Akio Fujii, Kamakura, all of Japan

[73] Assignee: Nippon Kayaku Kabushiki Kaisha, Tokyo, Japan

[21] Appl. No.: 928,551

[22] Filed: Nov. 10, 1986

[30] Foreign Application Priority Data

Nov. 15, 1985 [JP] Japan .................................. 60-254694
May 13, 1986 [JP] Japan .................................. 61-107589
May 16, 1986 [JP] Japan .................................. 61-110697

[51] Int. Cl.$^4$ .................. C07D 401/04; C07D 213/64; C07D 213/65
[52] U.S. Cl. ...................... 546/266; 546/182; 546/290; 546/348; 546/265
[58] Field of Search ................ 546/265, 266, 290, 348

[56] References Cited

FOREIGN PATENT DOCUMENTS 0095663 12/1983 European Pat. Off. ............ 514/706
0182317  5/1986 European Pat. Off. ............ 514/314
59-20274  2/1984 Japan .................................. 514/706

Primary Examiner—Alan L. Rotman
Attorney, Agent, or Firm—Banner, Birch, KcKie & Beckett

[57] ABSTRACT

This invention relates to the novel selenium compounds which are useful as an antineoplastic agent. The compounds are represented by the general formula (I):

$$Se(O)_a(R)_b(X)_c(A)_n(Y)_m \quad (I)$$

wherein R, X, A and Y represent the groups specified below, a represents a number of 0 or 1, b represents a number of 0, 1 or 2, and (1) when a is 0 and b is also 0, c is 4, n is 1 or 2 and m is 0, (2) when a is 1 and b is 0, c is 2, n is 1 or 2 and m is 0 or 1, and (3) when b is 1 or 2, c, n and m are all 0;

(i) when b is 2, R represents (1) a $C_{4-10}$ alkoxy group substituted with a halogen atom, (2) a lower alkoxyl group substituted with a halogen atom and a phenyl group, or (3) a cycloalkyloxy group substituted with a halogen atom, and (ii) when b is 1, R represents a group represented by the formula

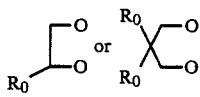

(wherein $R_0$ is a $C_{2-6}$ alkyl group);
X represents a halogen atom;
A represents a compound represented by the formula

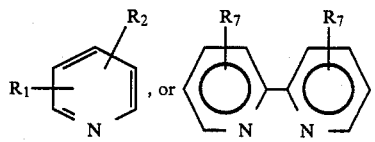

(wherein $R_1$ and $R_2$ may be the same or different and represent a hydrogen atom, a hydroxyl group, a lower alkyl group, a halogen atom, a phenyl group, a cyano group, a lower alkoxycarbonly group, a phenoxycarbonyl group, an amino group (to which a lower alkyl, lower alkylaminocarbonyl, lower halogenoalkylaminocarbonyl or lower alkoxycarbonyl group may be bonded), a benzoyl group, a loweralkoxyl group, a carbamyl group or an allyloxycarbonyl group;
$R_7$ represents a hydrogen atom, a lower alkyl group or a group represented by the formula

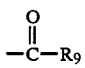

(wherein $R_9$ represents an amino group or a lowr alkoxyl group);
Y represents $H_2O$.

3 Claims, No Drawings

SELENIUM OXY CHLORIDE-PYRIDINE OR BIPYRIDINE COMPLEXES

1. BACKGROUND OF THE INVENTION

1. Field of the Invention

This invention relates to novel organic selenium compounds having antineoplastic activities.

2. Description of the Prior Art

It has already been reported that a certain type of selenium compounds have an antineoplastic or anticarcinogenic activity (see, for example Japanese Patent Kokai (Laid-Open) Nos. 20271/84 and EP-95663A).

However, no selenium compound has yet been found which is practically usable as an antineoplastic or anticancer agent.

SUMMARY OF THE INVENTION

The present invention relates to the novel selenium compounds represented by the general formula (I):

$$Se(O)_a(R)_b(X)_c(A)_n(Y)_m \qquad (I)$$

(wherein R, X, A and Y represent respectively the groups specified below, a represents a number of 0 or 1, b represents a number of 0, 1 or 2, and (1) when a is 0 and b is also 0, c is 4, n is 1 or 2, and m is 0, (2) when a is 1 and b is 0, c is 2, n is 1 or 2, and m is 0 or 1, and (3) when b is 1 or 2, c, n and m are all 0;
  (i) When b is 2, R represents (1) a $C_{4-10}$ alkoxy group substituted with a halogen atom, (2) a lower alkoxy group substituted with a halogen atom and a phenyl group, or (3) a cycloalkyloxy group substituted with a halogen atom, and (ii) when b is 1, R represents a group represented by the formula:

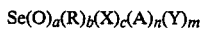

(wherein $R_0$ represents a $C_{2-6}$ alkyl group);
X represents a halogen atom;
A represents caffeine, theophylline, N-benzyltheophylline, N-benzyltheobromine, 2,2'-biquinoline, 1,6-naphthylidine, 1,10-phenanthroline or a compound represented by the formula:

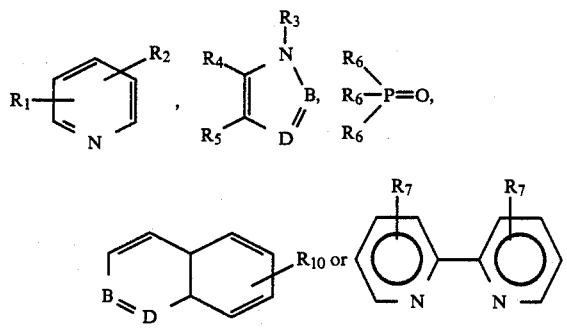

(wherein $R_1$ and $R_2$ may be the same or different and represent respectively a hydrogen atom, a hydroxyl group, a lower alkyl group, a halogen atom, a phenyl group, a cyano group, a lower alkoxycarbonyl group, a phenoxycarbonyl group, an amino group (to which a lower alkyl group, lower alkylaminocarbonyl group, lower halogenoalkylaminocarbonyl group or lower alkoxycarbonyl group may be bonded), a benzoyl group, a lower alkoxy group, a carbamyl group, or a allyloxycarbonyl group; $R_3$ represents a $C_{1-10}$ alkyl group or a benzyl group; $R_4$ and $R_5$ represent independently a hydrogen atom, a halogen atom or an alkyl group, or $R_4$ and $R_5$ may represent

in combination; $R_6$ represents a lower alkoxy group, a phenyl group or a phenoxy group; $R_7$ represents a hydrogen atom, a lower alkyl group or a group represented by the formula:

(wherein $R_9$ represents an amino group or a lower alkoxy group); $R_{10}$ represents a hydrogen atom or a nitro group; and one of B and D represents nitrogen and the other represents

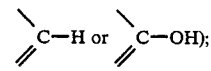

Y represents $H_2O$ or an alcohol represented by the formula: $R_8$-OH (wherein $R_8$ represents a benzyl or alkyl group which may be substituted with a lower alkoxyl group);
wherein when X is chlorine atom and m is 0, $R_1$ and $R_{10}$ represent an atom or a group other than hydrogen atom).

DETAILED DESCRIPTION OF THE INVENTION

In the above-shown general formula (I), the halogen atom can be fluorine, chlorine, bromine or iodine, but chlorine, bromine and fluorine are preferred. The lower alkyl group can be, for instance, a $C_{1-5}$ alkyl group such as methyl, ethyl, propyl, isopropyl, butyl, sec-butyl, t-butyl, pentyl and the like. As the alkyl group, $C_{1-10}$ alkyl groups such as methyl, ethyl, propyl, isopropyl, butyl, sec-butyl, t-butyl, pentyl, hexyl, octyl and decyl can be mentioned. The lower alkoxy group can be selected from $C_{1-5}$ alkoxy groups including methoxy, ethoxy, propoxy, isopropoxy and butoxy. The lower alkylamino group can be, for instance, a $C_{1-4}$ mono- or dialkylamino group. The cycloalkyloxy group can be selected from the $C_{4-8}$ cycloalkyloxy groups. The lower alkoxy in the lower alkoxycarbonyl group may be a $C_{1-5}$ lower alkoxy. The halogen in the lower halogenoalkylaminocarbonyl and lower halogenoalkyl groups can be fluorine, bromine, chlorine or iodine. The lower alkyl can be a $C_{1-5}$ lower alkyl.

In the compounds represented by the general formula (I), in case a is 1, b is 1 or 2, and c, m and n are 0, that is, in the case of SeO(R) $_1$ or 2, the $C_{4-10}$ alkoxyl group substituted with a halogen atom can be, for instance, 2-chlorobutoxy, 2-bromobutoxy, 2-chloropentyloxy, 2-bromopentyloxy, 2-chlorohexyloxy, 2-bromohexyloxy, 2-chloroheptyloxy, 2-bromoheptyloxy, 2-chlorooctyloxy, 2-bromooctyloxy, 2-chlorononanyloxy, 2-bromononanyloxy, 2-chlorodecanyloxy, 2-bromodecanyloxy, 2-chloro-1-methylethoxy, 2-chloro-1-methylpropoxy, 2-chloro-2-methylpropoxy, 2-chloro-1,1-dimethylpropoxy, 2-chloro-1,2-dimethylpropoxy, 2-chloro-1,1,2-trimethylpropoxy, 2-chloro-1-methylbutoxy, 2-chloro-2-methylbutoxy, 2-chloro-3-methylbutoxy, 2-chloro-1,1-dimethylbutoxy, 2-chloro-1,2-dimethylbutoxy, 2-chloro-1,2,3-trimethylbutoxy, 2-chloro-1,1,2,3-tetramethylbutoxy, 2-chloro-1,1,2,3,3-pentamethylbutoxy, 2-bromo-1-butylbutoxy and the like.

The lower alkoxy group substituted with a halogen atom and a phenyl group can be, for instance a $C_{2-4}$ alkoxy group such as 2-chloro-1-phenylethoxy, 2-chloro-2-phenylethoxy, 2-chloro-1-phenylpropoxy, 2-chloro-2-phenylpropoxy, 2-chloro-3-phenylpropoxy, and 2-bromo-2-phenylbutoxy.

Examples of the cycloalkyloxy groups substituted with a halogen atom are the $C_{4-8}$ cycloalkyloxy groups such as 2-chlorocyclobutyloxy, 2-chlorocyclopentyloxy, 2-chlorocyclohexyloxy, 2-chlorocyclooctyloxy, and 3-chloronorbonyl-2-iloxy. The $C_{2-6}$ alkyl groups represented by $R_0$ include ethyl, propyl, isopropyl, butyl, sec-butyl, t-butyl, pentyl and the like.

In the compounds represented by the general formula (I), in case b is 0, that is, in the case of the formula $Se(O)_a(X)_{2\ or\ 4}(A)_m(Y)_n$, the compounds represented by the formula

include pyridine, picoline, lutidine, ethylpyridine, isopropylpyridine, t-butylpyridine, phenylpyridine, fluoropyridine, chloropyridine, bromopyridine, dichloropyridine, cyanopyridine, ethyl picolinate, methyl nicotinate, ethyl nicotinate, methyl isonicotinate, ethyl isonicotinate, phenyl isonicotinate 4-benzoylpyridine, 4-aminopyridine, 4-dimethylaminopyridine, 2-N-methylaminopyridine, methyl 3-pyridiylcarboxamate, 2-hydroxypyridine, 4-hydroxypyridine, 4-methoxypyridine, allyl isonicotinate, N-methyl-N'-(3-pyridyl)-urea, N-(2-chloro)ethyl-N'-(3-pyridyl)urea, and 6-aminonicotinamide.

Examples of the compounds represented by the

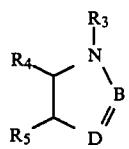

include N-methylimidazole, N-ethylimidazole, N-hexylimidazole, N-decylimidazole, N-benzylimidazole, 1,2-dimethylimidazole, 1-methyl-5-bromoimidazole, N-methylbenzimidazole, N-benzylbenzimidazole, 1-benzylpyrazole, and the like.

Examples of the compounds of the formula

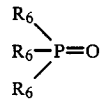

are triphenylphosphine oxide, triphenyl phosphate, trimethyl phosphate, triethyl phosphate and the like.

Examples of the compounds of the formula

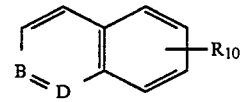

are isoquinoline, 1-hydroxyisoquinoline, 5-hydroxyisoquinoline, 5-nitroquinoline, 6-nitroquinoline, 8-nitroquinoline, 5-nitroisoquinoline and the like.

Examples of the compounds of the formula

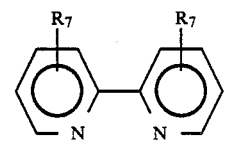

are 2,2'-dipyridyl, 2,2'-bi-methylisonicotinate, 2,2'-bi-ethylisonicotinate, 2,2'-bi-4-picoline and the like. Examples of the alcohols represented by Y are methyl alcohol, ethyl alcohol, propyl alcohol, octyl alcohol, benzyl alcohol, and anise alcohol.

As for the combinations of A and n, in case A is a 2,2'-dipyridyl derivative, 2,2'-biquinoline or 1,10-phenanthroline, n is 1, and in other cases, n is 1 or 2.

Typical examples of the compounds according to this invention are listed in Table 1 below.

TABLE 1-1

| Compound No. | Symbol | $SeO(R)_{1\ or\ 2}$ |
|---|---|---|
| 3-1 | SOC1P | Di-(2-chloro-1-methylpropyl)-selenite |
| 3-2 | SOC2P | Di-(2-chloro-2-methylpropyl)-selenite |
| 3-3 | SOCB | Di-(2-chlorobutyl)selenite |
| 3-4 | SOCO | Di-(2-chlorooctyl)selenite |
| 3-5 | SOPE | Di-(2-chlorophenetyl)selenite |
| 3-6 | SOCH | Di-(2-chlorcyclohexyl)selenite |
| 3-7 | SOCN | Di-(3-chloronorbonyl-2-il)selenite |
| 3-8 | SOEEC | 1,2-butanediolselenite |
| 3-9 | SOEPC | 2,2-diethyl-1,3-propanediolselenite |

TABLE 1-2

| Compound No. | Symbol | $SeO(X)_2(A)_m(Y)_n$ |
|---|---|---|
| 1-1 | SBPy | Selenium oxybromide-pyridine (1:2) complex |
| 1-2 | SC2Pc | Selenium oxychloride-2-picoline (1:2) complex |
| 3-3 | SC3Pc | Selenium olxychloride-3-picoline (1:3) complex |
| 1-4 | SC4Pc | Selenium oxychloride-4-picoline (1:2) complex |
| 1-5 | SC35Lt | Selenium oxychloride-3,5-lutidine (1:2) complex |
| 1-6 | SC4Et | Selenium oxychloride-4-ethylpyridine (1:2) complex |

TABLE 1-2-continued $SeO(X)_2(A)_m(Y)_n$

| Compound No. | Symbol | |
|---|---|---|
| 1-7 | SC4Ip | Selenium oxychloride-4-isopropyl-pyridine (1:2) complex |
| 1-8 | SC4Bt | Selenium oxychloride-4-t-butyl-pyridine (1:2) complex |
| 1-9 | SC2Ph | Selenium oxychloride-2-phenylpyridine (1:2) complex |
| 1-10 | SC3Ph | Selenium oxychloride-3-phenylpyridine (1:2) complex |
| 1-11 | SC4Ph | Selenium oxychloride-4-phenylpyridine (1:2) complex |
| 1-12 | SC3Fl | Selenium oxychloride-3-fluoropyridine (1:2) complex |
| 1-13 | SC3Cl | Selenium oxychloride-3-chloropyridine (1:2) complex |
| 1-14 | SC3Br | Selenium oxychloride-3-bromopyridine (1:2) complex |
| 1-15 | SC35DC | Selenium oxychloride-3,5-dichlor-pyridine (1:2) complex |
| 1-16 | SC3Cy | Selenium oxychloride-3-cyanopyridine (1:2) complex |
| 1-17 | SC4Cy | Selenium oxychloride-4-cyanopyridine (1:2) complex |
| 1-18 | SCPE | Selenium oxychloride-ethyl picolinate (1:2) complex |
| 1-19 | SCNM | Selenium oxychloride-methyl nicotinate (1:2) complex |
| 1-20 | SCNE | Selenium oxychloride-ethyl nicotinate (1:2) complex |
| 1-21 | SCIE | Selenium oxychloride-etyyl isonicotinate (1:2) complex |
| 1-22 | SCMIm | Selenium oxychloride-N—methyl-imidazole (1:2) complex |
| 1-23 | SCEIm | Selenium oxychloride-N—ethyl-imidazole (1:2) complex |
| 1-24 | SCHIm | Selenium oxychloride-N—hexyl-imidazole (1:2) complex |
| 1-25 | SCTIm | Selenium oxychloride-N—decylimidazole (1:2) complex |
| 1-26 | SCBIm | Selenium oxychloride-N—benzyl-imidazole (1:2) complex |
| 1-27 | SCDIm | Selenium oxychloride-1,2-dimethyl-imidazole (1:2) complex |
| 1-28 | SCRIm | Selenium oxychloride-1-methyl-5-bromo-imidazole (1:2) complex |
| 1-29 | SCMBi | Selenium oxychloride-N—methyl-benzimidazole (1:2) complex |
| 1-30 | SCBBi | Selenium oxychloride-N—benzyl-benzimidazole (1:2) complex |
| 1-31 | SCCf | Selenium oxychloride-caffein (1:2) complex |
| 1-32 | SBCf | Selenium oxybromide-caffein (1:2) complex |
| 1-33 | SCBTf | Selenium oxychloride-N—benzyl-theophylline (1:2) complex |
| 1-34 | SCBTb | Selenium oxychloride-N—benzyl-theobromine (1:2) complex |
| 1-35 | SCBPr | Selenium oxychloride-1-benzyl-pyrazole (1:2) complex |
| 1-36 | SCPP | Selenium oxycloride-triphenyl-phosphine oxide (1:2) complex |
| 1-37 | SCPOP | Selenium oxychloride-triphenyl phosphate (1:2) complex |
| 1-38 | SCMOP | Selenium oxychloride-trimethyl phosphate (1:2) complex |
| 1-39 | SCEOP | Selenium oxychloride-triethyl phosphate (1:2) complex |
| 1-40 | SClMBi | Selenium oxychloride-N–methylbenz-imidazole (1:1) complex |
| 1-41 | SCDp | Selenium oxychloride-2,2'-dipyridyl (1:1) complex |
| 1-42 | SBDp | Selenium oxybromide-2,2'-dipyridyl (1:1) complex |
| 1-43 | SCBPc | Selenium oxychloride-2,2'-bi-4-pyrroline (1:1) complex |
| 1-44 | SCBQn | Selenium oxychloride-2,2'-biquinoline (1:1) complex |
| 1-45 | SCPn | Selenium oxychloride-1,10-phenanthroline (1:1) complex |
| 1-46 | SCPy(M) | Selenium oxychloride-pyridine (1:2) complex mono methyl alcoholate |
| 1-47 | SCPy(E) | Selenium oxychloride-pyridine (1:2) complex mono ethyl alcoholate |
| 1-48 | SCPy(A) | Selenium oxychloride-pyridine (1:2) complex mono anise alcoholate |
| 1-49 | SCPy(O) | Selenium oxychloride-pyridine (1:2) complex mono octyl alcoholate |
| 1-50 | SCPy(B) | Selenium oxychloride-pyridine (1:2) complex mono benzyl alcoholate |
| 1-51 | SCIM | Selenium oxychloride-methyl iso-nicotinate (1:2) complex |
| 1-52 | SCIP | Selenium olxychloride-phenyl isonicotinate (1:2) complex |
| 3-10 | SC4Bz | Selenium oxychloride-4-benzyl-pyridine (1:2) complex |
| 3-11 | SC4Ap.aq | Selenium oxychloride-4-aminopyridine (1:2) complex mono hydrate |
| 3-12 | SC4MAp | Selenium oxychloride-4-dimethylamino-pyridine (1:2) complex |
| 3-13 | SC2Hy | Selenium oxychloride-2-hydroxypyridine (1:2) complex |
| 3-14 | SC4Hy.aq | Selenium oxychloride-4-hydroxypyridine (1:2) complex mono hydrate |
| 3-15 | SC4Mo | Selenium oxychloride-4-methoxy-pyridine (1:2) complex |
| 3-18 | SCIA | Selenium oxychloride-allyl iso-nicotinate (1:2) complex |
| 3-19 | SC16Np | Selenium oxychloride-1,6-naphthylidine (1:2) complex |
| 3-20 | SC5NQ | Selenium oxychloride-5-nitroquinoline (1:2) complex |
| 3-21 | SC6NQ | Selenium oxychloride-6-nitroquinoline (1:2) complex |
| 3-22 | SC8NQ | Selenium oxychloride-8-nitroquinoline (1:2) complex |
| 3-23 | SC5NI | Selenium oxychloride-5-nitroiso-quinoline (1:2) complex |
| 3-24 | SCTf | Selenium oxycloride-theophylline (1:2) complex |
| 3-25 | SCBIM | Selenium oxychloride-2,2'-bi-methyl-isonicotinate) (1:1) complex |
| 3-26 | SCBIE | Selenium oxychloride-2,2'-(ethyliso-nicotinate) (1:1) complex |
| 3-28 | SC2Ap.aq | Selenium oxychloride-2-aminopyridine (1:2) complex mono hydrate |
| 3-29 | SC25AAm | Selenium oxychloride-6-amino-nicotinamide (1:2) complex |
| 3-30 | SC25HN | Selenium oxychloride-2-hydroxy-5-nitropyridine (1:2) complex |
| 3-31 | SC4HQ | Selenium oxychloride-4-hydroxy-quinoline (1:2) complex |
| 3-32 | SC8HQ | Selenium oxychloride-8-hydroxy-quinoline (1:2) complex |
| 3-33 | SC4BI | Selenium oxychloride-4-bromoiso-quinoline (1:2) complex |
| 4-1 | SC3CUa.aq | Selenium oxychloride-3-(2-chloro-ethylaminocarbonylamino)pyridine (1:2) complex mono hydrate |
| 4-2 | SC2MAp.aq | Selenium oxychloride-2-(N—methylamino)-pyridine (1:2) complex mono hydrate |

TABLE 1-3

$SeX_4(A)_m$

| Compound No. | Symbol | |
|---|---|---|
| 2-1 | B4SPy | Tetrabromoselenium-pyridine (1:2) complex |
| 2-2 | C4S3Pc | Tetrachloroselenium-3-picoline (1:2) complex |
| 2-3 | C4S35Lt | Teltrachloroselenium-3,5-lutidine (1:2) complex |
| 2-4 | C4S3Ph | Tetrachloroselenium-3-phenylpyridine (1:2) complex |

TABLE 1-3-continued

| Compound No. | Symbol | $SeX_4(A)_m$ |
|---|---|---|
| 2-5 | C4S4Ph | Tetrachloroselenium-4-phenylpyridine (1:2) complex |
| 2-6 | C4S3Fl | Tetrachloroselenium-3-fluoropyridine (1:2) complex |
| 2-7 | C4S3Cy | Tetrachloroselenium-3-cyanopyridine (1:2) complex |
| 2-8 | C4S4Cy | Tetrachloroselenium-4-cyanopyridine (1:2) complex |
| 2-9 | C4SNM | Tetrachloroselenium-methyl nicotinate (1:2) complex |
| 2-10 | C4SIq | Tetrachloroselenium-isoquinoline (1:2) complex |
| 2-11 | C4SMI | Tetrachloroselenium-N—methylimidazole (1:2) complex |
| 2-12 | C4SCf | Tetrachloroselenium-caffein (1:2) complex |
| 2-13 | C4SDp | Tetrachloroselenium-2,2'-dipyridinyl (1:2) complex |
| 2-14 | B4SDp | Tetrabromoselenium-2,2'-dipyridyl (1:2) complex |

Among these compounds, the preferred ones are, for instance, 1-7, 1-10, 1-17, 1-28, 1-30, 1-41, 1-44, 1-46, 1-47, 2-1, 2-4, 2-5, 2-6, 2-7, 2-9, 3-2, 3-6, 3-9, 3-14, 3-18, 3-21, and 3-23. Most preferred are 1-41, and 3-14.

The compounds of this invention represented by the general formula (I) can be obtained from the following reaction:

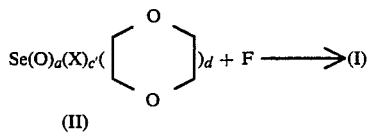

[wherein X represents a halogen atom; a is a number of 0 or 1, and when a is 0, c' is 4 and d is 0, and when a is 1, c' is 2 and d is 0 or 1; F represents A (where A is as defined above), a straight-chain 1,2-epoxyalkane, a lower 1,2-epoxyalkane substituted with a lower alkyl or phenyl group, an epoxycycloalkane, or a compound represented by the formula:

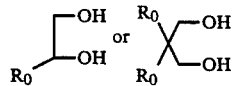

(wherein $R_0$ is as defined above)].

The compounds represented by the formula (II) include selenium oxyhalides such as selenium oxychloride, selenium oxybromide, etc., and their 1,4-dioxane complexes, and selenium tetrahalides such as tetrachloroselenium, tetrabromoselenium, etc. (The process for producing selenium oxyhalides dioxane (1:1) complex is described in the following literature; Yarovenko et al., Zh. Obshch. Khim. Vol. 31, P40006, 1961.)

The compounds represented by A in the formula F are such as mentioned before. The straight-chain 1,2-epoxyalkane can be a $C_{4-10}$ 1,2-epoxyalkane such as 1,2-epoxybutane, 1,2-epoxypentane, 1,2-epoxyhexane, 1,2-epoxyheptane, 1,2-epoxyoctane, 1,2-epoxynonane, and 1,2-epoxydecane.

Examples of the lower 1,2-epoxyalkanes substituted with a lower alkyl group are $C_{2-4}$ alkanes substituted with a lower alkyl group, such as 1,2-epoxypropane, 1-methyl-1,2-epoxypropane, 1,1-dimethyl-1,2-epoxypropane, 1,2-dimethyl-1,2-epoxypropane, 1,1,2-trimethyl-1,2-epoxypropane, 1-methyl-1,2-epoxybutane, 2-methyl-1,2-epoxybutane, 3-methyl-1,2-epoxybutane, 1,1-dimethyl-1,2-epoxybutane, 1,2-dimethyl-1,2-epoxybutane, 1,2,3-trimethyl-1,2-epoxybutane 1,1,2,3-tetramethyl-1,2-epoxybutane, 1,1,2,3,3-pentamethyl-1,2-epoxybutane, and 1-butyl-1,2-epoxybutane.

Examples of the lower 1,2-epoxyalkanes substituted with a phenyl group are $C_{2-4}$ 1,2-epoxyalkanes such as 1-phenyl-1,2-epoxyethane, 2-phenyl-1,2-epoxyethane, 1-phenyl-1,2-epoxypropane, 2-phenyl-1,2-epoxypropane, 3-phenyl-1,2-epoxypropane, and 2-phenyl-1,2-epoxybutane.

Examples of the epoxycycloalkane are $C_{4-8}$ 1,2-epoxycycloalkanes such as 1,2-epoxycyclobutane, 1,2-epoxycyclopentane, 1,2-epoxycyclohexane, 1,2-epoxycyclooctane, and 2,3-epoxynorbornane.

Examples of the compounds represented by the formula:

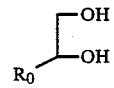

are 1,2-butanediol, 1,2-pentanediol, 1,2-hexanediol, and 1,2-octanediol.

Examples of the compounds represented by the formula:

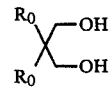

are 2,2-diethyl-1,3-propanediol, 2,2-propyl-1,3-propanediol, 2,2-diisopropyl-1,3-propanediol, 2,2-dibutyl-1,3-propanediol, and 2,2-dipentyl-1,3-propanediol.

For preparing the compounds of this invention, a compound represented by the formula (II) and a compound represented by the formula F are reacted, and if necessary, this reaction product is further reacted with water or an alcohol.

More specifically, the compounds of this invention represented by the general formula (I) can be obtained by reacting a compound represented by the formula (II) and a compound represented by the formula F in a solvent having a boiling point of 150° C. or below, preferably 110° C. or below, such as dioxane, hexane, chloroform, ether, methylene chloride, tetrahydrofuran and the like, at a temperature of preferably 0° to 100° C., more preferably 10° to 40° C., for a period of 30 minutes to 5 days, more preferably one hour to 3 days.

In this reaction, if a hydrous solvent is used, there is obtained a compound of the formula (I) where m is 1 and Y is $H_2O$, and if anhydrous alcohol-containing solvent is used, there is obtained a compound of the formula (I) where Y is an alcohol. In case an anhydrous non-alcoholic solvent is used, there is obtained a compound of the formula (I) where m is 0.

Further, the compounds of the formula (I) where a is 1, b is 1 or 2, and c, m and n are 0, namely, the compounds of the formula $SeO(R)_{1\ or\ 2}$ can be obtained in the following way.

(1) b=2:

A selenium oxyhalide-1,4-dioxane (1:1) complex or a selenium oxyhalide is reacted with a 1,2-epoxyalkane or 1,2-epoxycycloalkane which may be substituted with an alkyl or phenyl group, which corresponds to R in the above-shown formula, in an anhydrous solvent, and then the solvent is removed. As the solvent, those mentioned before can be used. The reaction is carried out at a temperature in the range of $-20°$ to $150°$ C., preferably $0°$ to $100°$ C., more preferably $10°$ to $40°$ C., for a period of 30 minutes to 24 hours, preferably 1 to 8 hours.

The amount of the 1,2-epoxyalkane or 1,2-epoxycycloalkane which may be substituted with an alkyl or phenyl group, which corresponds to R in the above-shown formula, should be exactly twice the amount of the starting material selenium oxyhalide-1,4-dioxane (1:1) complex or selenium oxyhalide.

(2) $b=1$.

A selencium oxyhalide or a selenium oxyhalide-1,4-dioxane (1:1) complex is reacted with a diol corresponding to R in the above formula in an anhydrous solvent. If this reaction is conducted in the presence of a metal salt of an organic carboxylic acid, preferably an aliphatic carboxylic acid or oxycarboxylic acid, for example, a sodium, potassium or silver salt of oxalic acid, citric acid, acetic acid, propionic acid or the like, the reaction proceeds smoothly. After the reaction ended, the solvent is removed after filtering out the precipitated metal salt in case a metal salt of an organic carboxylic acid was used.

The solvent used in this reaction may be those mentioned before. The reaction temperature is $-20°$ to $150°$ C., preferably $0°$ to $100°$ C., more preferably $10°$ to $40°$ C. The reaction time is 0.5 to 5 days, preferably 1 to 3 days.

As for the amount of the organic carboxylic acid and the diol used in the reaction, the former is preferably used in an amount approximately twice the amount of the starting selenium compound and the latter in an amount approximately equal to the amount of the selenium compound.

The compounds of the formula (I) where b and m are 0, that is, the compounds represented by the formula: $Se(O)_a(X)_{2\ or\ 4}(A)_{1\ or\ 2}$ can be obtained in the following way.

A selenium tetrahalide, a selenium oxyhalide or a selenium olxyhalide-1,4-dioxane (1:1) complex is reacted with a compound represented by A in the formula (I) in an anhydrous solvent, and then the solvent is removed.

The solvent used in this reaction may be those mentioned before. The reaction temperature is in the range of $-20°$ to $150°$ C., preferably $0°$ to $100°$ C., more preferably $10°$ to $35°$ C., and the reaction time is 30 minutes to 24 hours, preferably 1 to 8 hours.

The amount of A added is 1 to 10 times, preferably 2 to 3 times the amount of the starting selenium compound in case of obtaining the compounds of the formula (I) where $n=2$, and 0.5 to 5 times, preferably 1 to 2 times the amount of said selenium compound is case of obtaining the compounds of the formula (I) wherein $n=1$.

The compounds of the formula (I) where a is 1, b is 0, c is 2 and m is 1, that is, the compounds represented by the formula: $SeOX_2(A)_{1\ or\ 2}Y$ can be obtained by using a hydrous solvent or an anhydrous alcohol-containing solvent in the above-described reaction.

(1) The compounds of the above-shown formula where Y is $H_2O$ can be obtained by conducting the above-said reaction (for obtaining the compounds with $m=0$) by using a hydrous solvent with a water content of preferably 0.05 to 15%, more preferably 0.5 to 10%, or a hydrous alcohol solvent such as hydrous methanol with a water content of 0.5 to 10%, preferably 1 to 5%. In this case, the amount of the hydrous alcohol used, though variable depending on the water content, may be about 1 to 20% based on the solvent used for the reaction.

(2) The compounds of the above-shown formula where Y is an alcohol can be obtained by following said reaction process where m is 0 but by using an anhydrous solvent prepared by mixing an alcohol represented by Y and the above-said solvent.

The compounds of the above-shown formula where Y is $H_2O$ or an alcohol can be also obtained by reacting the compound of $m=0$ with water or an anhydrous alcohol. That is, water or an alcohol of the formula Y is added to the reaction solution used for synthesizing the compound of $m=0$, or the isolated compound of $m=0$ of the formula (I) is dissolved in water or an alcohol of the formula Y, or in a solvent containing water or an alcohol, preferably at $10°$ to $40°$ C. and allowed to stand as it is for 10 minutes to 2 hours, and then the solvent is removed. The amount of water or alcohol is not subject to any limitation as far as it is not less than one time the amount of the compound of $m=0$ of the formula (I), and its ratio can be selected merely according to the technical matter in carrying out the reaction.

Through the reactions described above, the objective compounds can be obtained as an oily product, amorphous powder, grease-like oily substance or crystal, and their structures were confirmed by IR and NMR analyses.

The determined property values of the typical examples of the compounds according to this invention are shown in Table 2.

TABLE 2

| Compound No. | Appearance | NMR (60 MHz) (Solvent A: chloroform-$d_1$ B: dimethyl sulfoxide-$d_6$) (ppm) | IR [KBr, (cm$^{-1}$)] |
|---|---|---|---|
| 1-1 | Yellow powder | A.: 8.19(m, 4H), 8.76(m, 2H), 9.07 (m, 4H) | 1641, 1607, 1537, 1488, 904, 752, 678 |
| 1-2 | Light-yellow powder, hygroscopic | A.: 2.66(s, 6H), 7.53–7.76(m, 4H) 8.07–8.36(m, 2H), 8.69(br d, j=5.2Hz, 2H) | 1638, 1624, 1546 1480, 890, 764, 700, 660 |
| 1-3 | White powder, hygroscopic | A.: 2.46(s, 6H), 7.77(dd, J=8.0, 5.4Hz, 2H), 8.21(brd, j=8.0Hz, 2H), 8.68 (br d, J=5.4Hz, 2H), 8.73(br s, 2H) | 1638, 1620, 1559 1480, 895, 792, 677 |
| 1-4 | White powder, hygroscopic | A.: 2.69(s, 6H), 7.96(brd, J=6.2Hz, 4H), 8.83 (br d, J=6.2Hz, 4H) | 1645, 1613, 1512, 1204, 895, 793, 705, 660 |
| 1-5 | White | A.: 2.48(s, 12H), 8.34(br s, 2H), 8.68 | 2070, 1630, 1571, |

TABLE 2-continued

| Compound No. | Appearance | NMR (60 MHz) (Solvent A: chloroform-d$_1$ B: dimethyl sulfoxide-d$_6$) (ppm) | IR [KBr, (cm$^{-1}$)] |
|---|---|---|---|
| | powder, hygroscopic | (br s, 4H) | 1275, 890, 860, 725, 680 |
| 1-6 | White powder, hygroscopic | A.: 1.27(d, J=7.6Hz, 6H), 2.93 (q, J=7.6Hz, 4H), 7.99 (br d, J=6.4Hz, 4H), 8.87(br d, J=6.4Hz, 4H) | 1645, 1608, 1508, 1205, 890, 822, 774, 650 |
| 1-7 | White powder, hygroscopic | A.: 1.27(d, J=7.0Hz, 12H), 3.14 (septet, J=7Hz, 2H), 7.82 (br d, J=6.0Hz, 4H), 8.76(br d, J=6.0Hz, 4H) | 1644, 1610, 1509, 1208, 1060, 892, 820, 656 |
| 1-8 | White powder, hygroscopic | A.: 1.38(s, 18H), 8.04(br d, J=6.0Hz, 4H), 8.84(br d, J=6.0Hz, 4H) | 1644, 1610, 1508, 931, 880, 843, 819, 656 |
| 1-9 | Yellow oil viscous | A.: 7.45–7.78(m, 8H), 8.03–8.21(m, 8H), 8.79(ddd, J=4.8, 1.2, 1.2Hz, 2H) | 1618, 1583, 1540, 1501, 1472, 1441, 1393, 1278, 906, 840, 795, 757, 730, 691 |
| 1-10 | White powder, hygroscopic | A.: 7.52–8.09(m, 12H), 8.69(ddd, J=8.0 2.4, 1.6Hz, 2H), 8.78 (br d, J=4.8Hz, 2H), 9.21(br s, 2H) | 1624, 1558, 1502, 1474, 1446, 893, 818, 758, 694, 680 |
| 1-11 | White powder, hygroscopic | A.: 7.62–7.72(m, 6H), 7.94–8.17(m, 4H), 8.42(br d, J=7.2Hz, 4H), 9.01 (br d, J=7.2Hz, 4H) | 1640, 1606, 1599, 1523, 1489, 1293 877, 848, 837, 824, 760 |
| 1-12 | Yellow oil | A.: 7.58–7.95(m, 2H), 8.12(ddd, J=8.6, 3.0, 1.4Hz, 2H), 8.64 (br d, J=4.4Hz, 2H), 8.83(br s, 2H) | 1616, 1553, 1477, 1242, 895, 839, 826, 807, 668 |
| 1-13 | Light-yellow fine crystal, hygroscopic | A.: 7.66(dd, J=8.4, 4.8Hz, 2H), 8.18 (ddd, J=8.4, 2.4, 1.4Hz, 2H), 8.6–8.9(m, 4H) | 1625, 1532, 1460, 1125, 890, 800, 730, 665 |
| 1-14 | Light-yellow fine crystal | A.: 7.60(dd, J=8.0, 4.8Hz, 2H), 8.30 (ddd, J=8.0, 2.4, 1.4Hz, 2H), 8.74 (br d, J=4.8Hz, 2H), 8.92(br s, 2H) | 1620, 1595, 1520, 1464, 1452, 1246, 1108, 1015, 884, 857, 790, 664 |
| 1-15 | White fine crystal | B.: 7.87(t, J=2.1Hz, 2H), 8.61(d, J=2.1Hz, 4H) | 1536, 1417, 1250, 1121, 1108, 911, 848, 821, 687, 658 |
| 1-16 | White crystal | A.: 7.71(ddd, J=7.9, 4.8, 0.9Hz, 2H), 8.39(ddd, J=7.9, 1.9, 1.8Hz, 2H), 8.91(br d, J=4.8Hz, 2H), 9.07(br s, 2H) | 2254, 1639, 1611, 1558, 1465, 904, 837, 810, 771, 730, 678, 669 |
| 1-17 | Light-yellow crystal | A.: 7.95(dd, J=4.4, 1.6Hz, 4H), 8.90 (br d, J=4.4Hz, 4H) | 2250, 2088, 2006, 1638, 1598, 1499, 1338, 1303, 1235, 1006, 899, 882, 820, 665 |
| 1-18 | Yellow oil | A.: 1.35(t, J=7.0Hz, 6H), 4.38(q, J=7.0Hz, 4H), 7.58–7.93(m, 2H), 8.03–8.14(m, 4H), 8.75(br d, J=4.2Hz, 2H) | 1745, 1611, 1537, 1459, 1332, 1291, 1160, 1008, 901, 861, 750, 675 |
| 1-19 | White fine crystal hygroscopic | A.: 3.98(s, 6H), 7.89(br dd, J=8.8, 4.8Hz, 2H), 8.63(ddd, J=8.0, 2.0, 1.8Hz, 2H), 9.03(br d, J=4.8Hz, 2H), 9.27(br s, 2H) | 1747, 1735, 1640, 1612, 1542, 1468, 1457, 1438, 1300, 1135, 1112, 956, 907, 883, 832, 740, 692, 671 |
| 1-20 | Light-yellow oil | A.: 1.36(t, J=7.0Hz, 6H), 4.41(q, J=7.0Hz, 4H), 7.85(br dd, J=8.0, 4.8Hz, 2H), 8.59(ddd, J=8.0, 2.0, 1.8Hz, 2H), 8.98(br d, J=4.8Hz, 2H), 9.21(br s, 2H) | 1735, 1640, 1610, 1470, 1375, 1300, 1136, 1112, 1018, 897, 868, 832, 740, 690, 671 |
| 1-21 | Light-yellow fine crystal | A.: 1.38(t, J=7.0Hz, 6H), 4.44(q, J=7.0Hz, 4H), 8.22(dd, J=4.8, 1.6Hz, 4H), 9.05(br d, J=4.8Hz, 4H) | 1735, 1605, 1510, 1319, 1296, 1235, 874, 859, 846, 775, 684 |
| 1-22 | Light-yellow powder hygroscopic | A.: 3.88(s, 6H), 7.59(br s, 2H), 7.65 (br s, 2H), 8.93(br s, 2H) | 1580, 1548, 1440, 1280, 1084, 890, 820, 750, 655 |
| 1-23 | White fine crystal, hygroscopic | A.: 1.51(t, J=7.2Hz, 6H), 4.18(q, J=7.2Hz, 4H), 7.13(br s, 2H), 7.33 (br s, 2H), 8.36(br s, 2H) | 1581, 1552, 1453, 1298, 1094, 896, 824, 758, 655 |
| 1-24 | White powder, hygroscopic | B.: 0.8–1.2(m, 6H), 1.2–1.7(m, 12H), 1.83(m, 4H), 4.16(t, J=7.4Hz, 4H), 7.11(br s, 2H), 7.35(br s, 2H), 8.55 (br s, 2H) | 1568, 1550, 1463, 1287, 1089, 890, 840, 760 |
| 1-25 | Light-yellow powder, hygroscopic | B.: 0.7–1.1(m, 6H), 1.1–1.6(m, 28H), 1.87(m, 4H), 4.27(t, J=7.2Hz, 4H), 7.17(br s, 2H), 7.46(br s, 2H), 9.14 (br s, 2H) | 1578, 1551, 1468, 1315, 1290, 1095, 890, 840, 805, 763 |
| 1-26 | White powder, hygroscopic | B.: 5.50(s, 4H), 7.16(br s, 2H), 7.42(br s, 12H), 9.44(br s, 2H) | 1577, 1548, 1460, 1280, 1087, 890, 840, 825, 780, 760, 710 |

TABLE 2-continued

| Compound No. | Appearance | NMR (60 MHz) (Solvent A: chloroform-d$_1$ B: dimethyl sulfoxide-d$_6$) (ppm) | IR [KBr, (cm$^{-1}$)] |
|---|---|---|---|
| 1-27 | White fine powder, hygroscopic | B.: 2.60(s, 6H), 3.77(s, 6H), 7.52(d, J=2.0Hz, 2H), 7.61(d, J=2.0Hz, 2H) | 1610, 1542, 1445, 1287, 930, 900, 755, 650 |
| 1-28 | Light-brown powder, hygroscopic | B.: 3.96(s, 6H), 7.65(br s, 2H), 9.53(br s, 2H) | 1566, 1555, 1304, 1106, 910, 825, 676 |
| 1-29 | White powder, hygroscopic | B.: 4.03(s, 6H), 7.2–7.6(m, 6H), 7.7–8.0 (m, 2H), 9.04(br s, 2H) | 1567, 1462, 1442, 1154, 1135, 891, 865, 850, 820, 778, 749 |
| 1-30 | White powder | B.: 5.68(s, 4H), 7.37(s, 10H), 7.2–7.6 (m, 6H), 7.8–8.2(m, 2H), 9.57(br s, 2H) | 1550, 1450, 1378, 897, 845, 812, 773, 743, 717, 697 |
| 1-31 | White fine crystal hygroscopic | B.: 3.43(s, 6H), 3.65(s, 6H), 4.07(s, 6H), 7.90(s, 2H) | 1706, 1680, 1670, 1660, 1580, 1556, 1490, 1425, 980, 925, 870, 760, 745 |
| 1-32 | Yellow powder | B.: 3.42(s, 6H), 3.65(s, 6H), 3.97(s, 6H), 7.66(s, 2H) | 1705, 1680, 1670, 1660, 1576, 1554, 1488, 1440, 980, 930, 860, 759, 745 |
| 1-33 | Light-yellow fine crystal | B.: 3.42(s, 6H), 3.63(s, 6H), 5.61(s, 4H), 7.40(s, 10H), 7.97(s, 2H) | 1709, 1670, 1550, 1452, 1377, 1233, 1029, 877, 860, 761, 750, 732, 692 |
| 1-34 | Light-yellow powder | B.: 3.61(s, 6H), 4.04(s, 6H), 5.18(s, 4H), 7.1–7.6(m, 10H), 7.97(s, 2H) | 1708, 1687, 1668, 1555, 1438, 951, 928, 892, 872, 830, 759, 743, 724, 699 |
| 1-35 | Light-yellow oil | B.: 5.57(s, 4H), 6.44(dd, J=2.3, 2.2Hz, 2H), 7.37(s, 10H), 7.53(d, J=2.3Hz, 2H), 7.82(d, J=2.0Hz, 2H) | 1501, 1456, 1440, 1419, 1102, 920, 903, 779, 708 |
| 1-36 | Light-yellow powder, hygroscopic | B.: 7.35–7.90(m, 30H) | 1590, 1486, 1438, 1100, 1066, 1024, 996, 935, 724, 717, 685 |
| 1-37 | White fine crystal hygroscopic | B.: 7.29(m, 30H) | 1592, 1487, 1298, 1200, 1183, 1166, 1013, 965, 957, 935, 770, 690 |
| 1-38 | Colorless oil | B.: 3.78(d, J=11.2Hz, 18H) | 1452, 1240, 1192, 1045, 952, 855, 750, 695 |
| 1-39 | Light yellow oil | B.: 1.35(t, J=6.7Hz, 18H), 4.14(dq, J=7.8, 6.7Hz, 12H) | 1484, 1450, 1400, 1375, 1295, 1230, 1172, 1005, 1035, 985, 830, 805 |
| 1-40 | Light yellow powder, hygroscopic | B.: 4.25(s, 3H), 7.4–7.8(m, 3H), 7.8–8.1(m, 1H), 10.0(s, 1H) | 1618, 1601, 1565, 1461, 1449, 1348, 1272, 1158, 1138, 1106, 870, 854, 758, 687, 655 |
| 1-41 | Light yellow fine crystal, hygroscopic | A.: 7.91(ddd, J=7.2, 5.0, 1.5Hz, 2H), 8.44(ddd, J=8.0, 7.2, 1.7Hz, 2H), 8.75(br d, J=8.0Hz, 2H), 8.94(br d, J=5.0Hz, 2H) | 1625, 1605, 1590, 1535, 1439, 1290, 1180, 920, 890, 862, 780, 758 |
| 1-42 | White powder | A.: 7.94(ddd, J=7.3, 5.0, 1.2Hz, 2H), 8.35 (ddd, J=7.8, 7.3, 1.6Hz, 2H), 8.66(br d, J=7.8Hz, 2H), 8.97(br d, J=5.0Hz, 2H) | 1625, 1608, 1587, 1532, 1460, 1438, 1181, 923, 890, 865, 762 |
| 1-43 | White fine crystal | A.: 2.63(s, 6H), 7.82(br d, J=5.4Hz, 2H), 8.67(br s, 2H), 8.82(d, J=5.4Hz, 2H) | 1625, 1604, 1509, 1435, 1296, 1222, 1120, 858, 826, 664 |
| 1-44 | Yellow fine crystal | A.: 7.62–8.41(m, 8H), 8.70(d, J=8.8Hz, 2H), 8.89(d, J=8.8Hz, 2H) | 1635, 1604, 1540, 1511, 1385, 1218, 934, 889, 872, 830, 744 |
| 1-45 | White powder | A.: 8.28(dd, J=8.0, 4.8Hz, 2H), 8.40(s, 2H), 9.16(dd, J=8.0, 1.6Hz, 2H), 9.37(dd, J=4.8, 1.6Hz, 2H) | 1620, 1598, 1548, 1470, 950, 885, 876, 849, 716, 696 |
| 1-46 | Light yellow greasy oil | A.: 3.44(s, 3H), 8.10–8.35(m, 4H), 8.64–8.95(m, 2H), 9.09(dd, J=6.2, 1.2Hz, 4H) | 1640, 1610, 1537, 1490, 912, 864, 745, 673 |
| 1-47 | Light yellow greasy oil | A.: 1.13(t, J=7.0Hz, 3H), 3.72(q, J=7.0Hz, 2H), 8.00–8.26(m, 4H), 8.53–8.85(m, 2H), 8.99(dd, J=6.0, 1.2Hz, 4H) | 1642, 1609, 1539, 1490, 910, 870, 747, 677 |
| 1-48 | Brown greasy oil | A.: 3.76(s, 3H), 4.73(br s, 2H), 6.90 (d, J=8.6Hz, 2H), 7.31(d, J=8.6Hz, 2H), 7.96–8.21(m, 4H), 8.48–8.79 (m, 2H), 8.96(dd, J=6.4, 1.2Hz, | 1640, 1616, 1531, 1520, 1490, 1252, 1180, 1031, 908, 850, 820, 748, 675 |

TABLE 2-continued

| Compound No. | Appearance | NMR (60 MHz) (Solvent A: chloroform-d$_1$ B: dimethyl sulfoxide-d$_6$) (ppm) | IR [KBr, (cm$^{-1}$)] |
|---|---|---|---|
| | | 4H) | |
| 1-49 | Light brown greasy oil | A.: 0.7–1.1(m, 3H), 1.1–1.7(m, 12H), 3.79(m, 2H), 7.94–8.20(m, 4H), 8.47–8.79(m, 2H), 8.95(dd, J=6.2, 1.2Hz) | 1639, 1614, 1602, 1531, 1482, 1058, 1050, 907, 748, 677 |
| 1-50 | Yellow greasy oil | A.: 4.91(br s, 2H), 7.43(m, 5H), 8.00–8.25(m, 4H), 8.53–8.84(m, 2H), 9.03(br d, J=5.2Hz, 4H) | 1640, 1615, 1606, 1540, 1532, 1491, 908, 747, 675 |
| 1-51 | Light yellow fine crystal | A.: 3.99(s, 6H), 8.13(dd, J=4.4, 1.6Hz, 4H), 9.03(br d, J=4.4Hz, 4H) | 1734, 1610, 1514, 1430, 1299, 1121, 868, 849, 830, 754, 692 |
| 1-52 | Light brown fine crystal | A.: 7.2–7.7(m, 10H), 8.21(dd, J=4.4, 1.6Hz, 4H), 9.00(br dd, J=4.4, 1.6Hz, 4H) | 1750, 1599, 1488, 1281, 1272, 1191, 914, 845, 749, 696, 681 |
| 2-1 | Red powder | B.: 8.37(br dd, J=7.6, 6.4Hz, 4H), 8.55–8.86(m, 2H), 9.27(dd, J=6.4 1.6Hz, 4H) | 1637, 1600, 1532, 1481, 1324, 1195, 1045, 902, 873, 850, 740, 675 |
| 2-2 | Yellow powder | B.: 3.51(s, 6H), 7.94(br dd, J=8.0, 5.6Hz, 2H), 8.44(br d, J=8.0Hz, 2H), 8.76(br d, 5.6Hz, 2H), 8.81 (br s, 2H) | 1633, 1618, 1558, 1475, 1390, 1268, 1185, 1121, 888, 822, 783, 673 |
| 2-3 | Yellow powder | B.: 2.45(s, 12H), 8.23(br s, 2H), 8.60(br s, 4H) | 1631, 1558, 1470, 1385, 1328, 1274, 1264, 920, 846, 817, 721, 670 |
| 2-4 | Yellow powder, hygroscopic | B.: 7.53–7.70(m, 6H), 7.82–8.03(m, 4H), 8.16(m, 2H), 8.90–9.08(m, 4H), 9.32(d, J=1.6Hz, 2H) | 1610, 1548, 1500, 1471, 1441, 1347, 1265, 1115, 918, 788, 737, 684, 653 |
| 2-5 | Yellow powder | B.: 7.56–7.72(m, 6H), 7.88–8.11(m, 4H), 8.42(m, 4H), 8.98(m, 4H) | 1636, 1593, 1486, 1290, 1212, 1066, 1007, 812, 756, 715, 682 |
| 2-6 | Yellow powder, hygroscopic | B.: 7.86(m, 2H), 8.23(m, 2H), 8.69(m, 2H), 8.94(m, 2H) | 1550, 1477, 1280, 1245, 1108, 917, 830, 801, 766, 660 |
| 2-7 | Yellow fine crystal | B.: 7.68(ddd, J=8.0, 5.2, 0.8Hz, 2H), 8.39(ddd, J=8.0, 2.0, 1.6Hz, 2H), 8.88(dd, J=5.2, 2.0Hz, 2H), 9.06(dd, J=1.6, 0.8Hz, 2H) | 2256, 1639, 1605, 1548, 1463, 1187, 1118, 898, 801, 777, 670 |
| 2-8 | Orange powder, hygroscopic | B.: 8.11(dd, J=5.3, 1.1Hz, 4H), 8.98(br d, J=5.3Hz, 4H) | 2250, 1642, 1608, 1507, 1362, 1250, 1228, 1215, 1007, 901, 802 |
| 2-9 | Orange gum, hygroscopic | B.: 3.94(s, 6H), 7.96(br dd, J=7.4, 4.2Hz, 2H), 8.71(br d, J=7.4Hz, 2H), 9.01(br d, J=4.2Hz, 2H), 9.22(br s, 2H) | 1745, 1640, 1604, 1541, 1464, 1434, 1298, 1193, 1135, 1114, 954, 859, 826, 734, 690, 670 |
| 2-10 | Yellow powder | B.: 7.88–8.80(m, 12H), 9.96(br s, 2H) | 1642, 1611, 1578, 1540, 1488, 1392, 1371, 932, 795, 759, 736 |
| 2-11 | Yellow powder, hygroscopic | B.: 3.89(br s, 6H), 7.64–7.71(m, 4H), 9.14(br s, 2H) | 1585, 1554, 1438, 1282, 1085, 914, 848, 810, 757 |
| 2-12 | Yellow powder, hygroscopic | B.: 3.21(s, 6H), 3.40(s, 6H), 3.88(s, 6H), 8.03(br s, 2H) | 1715, 1680, 1650, 1578, 1552, 1440, 970, 878, 795, 758, 743, 725 |
| 2-13 | Yellow powder hygroscopic | B.: 7.91(ddd, J=7.2, 5.2, 1.4Hz, 2H), 8.42(ddd, J=7.6, 7.2, 1.6Hz, 2H), 8.74(br d, J=7.6Hz, 2H), 8.90(br d, J=5.2Hz, 2H) | 1614, 1601, 1528, 1445, 1290, 950, 934, 761 |
| 2-14 | Brown powder | B.: 7.83–8.95(m, 2H), 8.33–8.61(m, 2H), 8.82(br d, J=7.0Hz, 2H), 9.02(br d, J=5.0Hz, 2H) | 1603, 1586, 1532, 1446, 1433, 1314, 1174, 1018, 923, 759 |
| 3-1 | Light yellow oil | B.: 1.13(d, J=6.0Hz, 6H), 1.40(d, J=6.4Hz, 6H), 3.52–4.23(m, 4H) | 1387, 1264, 1108, 1012, 891, 859, 782, 668 |
| 3-2 | Yellow oil | B.: 1.49(s, 12H), 3.44(s, 4H) | 1392, 1377, 1270, 1148, 1108, 972, 920, 869, 770, 664 |
| 3-3 | Yellow oil | B.: 0.71–1.08(m, 6H), 1.2–2.0(m, 4H), 3.4–3.6(m, 4H), 3.6–4.1(m, 2H) | 1262, 1112, 857, 685, 664 |
| 3-4 | Light | B.: 0.87(br t, J=5.0Hz, 6H), | 1467, 1382, 1268, |

TABLE 2-continued

| Compound No. | Appearance | NMR (60 MHz) (Solvent A: chloroform-$d_1$ B: dimethyl sulfoxide-$d_6$) (ppm) | IR [KBr, (cm$^{-1}$)] |
|---|---|---|---|
| | yellow oil | 1.3(br s, 20H), 3.45–3.78(m, 4H), 3.8–4.2(m, 2H) | 1110, 1088, 1059, 920, 856, 666 |
| 3-5 | Yellow oil, viscous | B.: 3.98(d, J=6.6Hz, 4H), 5.13(t, J=6.6Hz, 2H), 7.46(m, 10H) | 1498, 1457, 1067, 1030, 973, 937, 914, 847, 760, 722, 695, 660 (oil film) |
| 3-6 | Light yellow oil, viscous | B.: 1.2–2.3(m, 16H), 3.4–4.5(m, 4H) | 1453, 1130, 1080, 1012, 961, 925, 900, 869, 848, 736, 660 (oil film) |
| 3-7 | Yellow oil, viscous | B.: 0.89–2.16(m, 16H), 3.7–4.3(m, 4H) | 1352, 1149, 1078, 1013, 998, 917, 902, 856, 692, 658 |
| 3-8 | Colorless oil | A.: 1.06(br t, J=3.3Hz, 3H), 1.5–2.1(m, 2H), 3.8–5.1(m, 3H) | 1465, 1385, 1354, 1334, 1223, 1108, 1081, 1059, 1030, 1012, 984, 931, 848, 775, 715, 664, (oil film) |
| 3-9 | Light yellow oil, viscous | A.: 0.91(t, J=7.6Hz, 6H), 1.82(J=7.6Hz, 4H), 3.61(br d, J=12.0Hz, 2H), 4.77(br d, J=12.0Hz, 2H) | 1465, 1387, 1063, 993, 936, 922, 900 |
| 3-10 | Light yellow powder | B.: 7.4–8.1(m, 10H), 8.05(dd, J=4.4, 1.8Hz, 4H), 9.04(dd, J=4.4, 1.6Hz, 4H) | 1678, 1601, 1330, 1316, 1285, 948, 932, 842, 786, 742, 720, 693 |
| 3-11 | White powder, hygroscopic | B.: 6.96(br d, J=7.3Hz, 4H), 8.18(br d, J=7.3Hz, 4H), 8.36(br s, 2H), 9.58(br, s, 4H) | 1660, 1600, 1535, 1197, 996, 850, 806 |
| 3-12 | White powder | B.: 3.22(s, 12H), 7.02(m, 4H), 8.26(m, 4H) | 1652, 1565, 1217, 999, 944, 913, 899, 882, 853, 807 |
| 3-13 | Light yellow powder, hygroscopic | B.: 6.52–6.82(m, 4H), 7.65–7.96(m, 4H), 13.66(s, 2H) | 1640, 1543, 1372, 1338, 1165, 1101, 994, 860, 820, 772, 725 |
| 3-14 | White fine crystal | B.: 7.32(m, 4H), 8.52(m, 4H), 11.3–12.8(br s, 4H) | 1647, 1614, 1535, 1517, 1390, 1378, 1327, 1225, 1196, 850, 816 |
| 3-15 | White fine crystal | B.: 4.13(s, 6H), 7.61(m, 4H), 8.83(m, 4H) | 1640, 1602, 1532, 1515, 1325, 1307, 1198, 1013, 993, 830 |
| 3-18 | Yellowish brown oil, greasy | B.: 4.81–4.93(m, 4H), 5.19–5.59(m, 4H), 5.79–6.41(m, 2H), 8.10(dd, J=4.8, 1.4Hz, 4H), 8.95(br d, J=4.8Hz, 4H) | 1738, 1645, 1608, 1323, 1285, 1237, 1133, 939, 845, 756, 683 |
| 3-19 | Light brown powder | B.: 8.10(dd, J=9.0, 4.6Hz, 2H), 8.52(d, J=6.2Hz, 2H), 9.08(d, J=6.2Hz, 2H), 9.10(dd, J=9.0, 1.6Hz, 2H), 9.56(dd, J=4.6, 1.6Hz, 2H), 10.11(s, 2H) | 1658, 1610, 1556, 1496, 1444, 1331, 1292, 1277, 839, 819 |
| 3-20 | Yellow fine crystal | B.: 7.87(dd, J=8.6, 4.2Hz, 2H), 8.02(dd, J=8.8, 7.8Hz, 2H), 8.47(br d, J=7.8Hz, 2H), 8.50(br d, J=8.8Hz, 2H), 8.93(br d, J=8.6Hz, 2H), 9.14(dd, J=4.2, 1.6Hz, 2H) | 1639, 1614, 1598, 1535, 1371, 1346, 1305, 1238, 1221 1199, 1148, 1000, 878, 858, 805, 729, 687, 662 |
| 3-21 | Light yellow powder | B.: 7.85(dd, J=8.4, 4.4Hz, 2H), 8.28 (d, J=9.2Hz, 2H), 8.55(dd, J=9.2, 2.4Hz, 2H), 8.89(br d, J=8.4Hz, 2H), 9.13–9.28(m, 4H) | 1647, 1608, 1557, 1540, 1486, 1386, 1357, 1305, 1128, 907, 901, 858, 809, 766, 659 |
| 3-22 | Orange powder | B.: 7.72–7.98(m, 4H), 8.33–8.47(m, 4H), 8.69(dd, J=8.2, 1.8Hz, 2H), 9.15 (dd, J=4.2, 1.8Hz, 2H) | 1641, 1598, 1535, 1352, 1277, 1268, 1190, 877, 842, 832, 788, 759 |
| 3-23 | Light yellow powder | B.: 8.04(dd, J=8.0, 7.6Hz, 2H), 8.56 (br d, J=6.4Hz, 2H), 8.71–8.90(m, 6H), 9.81(br s, 2H) | 1657, 1621, 1582, 1532, 1487, 1341, 1267, 880, 859, 817, 793, 668 |
| 3-24 | White powder | B.: 3.40(s, 6H), 3.62(s, 6H), 5.4–5.7 (br s, 2H), 8.43(s, 2H) | 1725, 1674, 1570, 1446, 1195, 982, 741 |
| 3-25 | Yellow gum | A.: 4.10(s, 6H), 8.36(dd, J=5.2, 1.6Hz, 2H), 9.17(br s, 2H), 9.20(br d, J=5.2Hz, 2H) | 1739, 1440, 1363, 1300, 1267, 1250, 1129, 962, 758, 721, 695 |
| 3-26 | Yellow gum | A.: 1.51(t, J=7.2Hz, 6H), 4.58(d, J=7.2Hz, 4H), 8.29(dd, J=5.2, 1.6Hz, 2H), 9.19(br s, 2H), 9.29(br d, J=5.2Hz, 2H) | 1735, 1377, 1368, 1293, 1259, 1141, 1112, 1021, 759, 689 |

TABLE 2-continued

| Compound No. | Appearance | NMR (60 MHz) (Solvent A: chloroform-d$_1$ B: dimethyl sulfoxide-d$_6$) (ppm) | IR [KBr, (cm$^{-1}$)] |
|---|---|---|---|
| 3-28 | Yellow oil, viscous | B.: 3.34(br s, 2H), 6.95–7.37(m, 4H), 8.01–8.31(m, 4H), 8.5(br s, 4H) | 1662, 1620, 1548, 1478, 1380, 1326, 1241, 1166, 995, 881, 763 (oil film) |
| 3-29 | White fine crystal | B.: 7.08(d, J=9Hz, 2H), 7.61(br s, 2H), 8.22(br s, 2H), 8.31(dd, J=9 and 2Hz, 2H), 8.54(d, J=2Hz, 2H), 8.6(br, 4H), [FT-NMR (400MHz)] | 1700–1652, 1631, 1597, 1554, 1485, 1426, 1400, 1356, 1255, 1164, 1143, 1053, 857, 834, 771, 739 |
| 3-30 | White needle crystal | B.: 6.48(d, J=10.2Hz, 2H), 8.20(dd, J=10.2, 3.2Hz, 2H), 8.48(br s, 2H), 8.72(d, J=3.2Hz, 2H) | 1675, 1600, 1639, 1571, 1510, 1434, 1351, 1254, 1123, 917, 888, 835, 759, 716, (nujol) |
| 3-31 | White fine crystal | B.: 7.25(d, J=7Hz, 2H), 7.76(dd, J=8 and 7Hz, 2H), 8.03(dd, J=8 and 7Hz, 2H), 8.13(d, J=8Hz, 2H), 8.32(d, J=8Hz, 2H), 8.80(d, J=7Hz, 2H), [FT-NMR (400MHz)] | 1646, 1620, 1591, 1500, 1412, 1350, 1306, 876, 829, 781, 759 |
| 3-32 | Yellow powder | B.: 7.59(d, J=5Hz, 2H), 7.76–7.79(m, 4H), 8.05(dd, J=8 and 5Hz, 2H), 9.11 (d, J=5Hz, 2H), 9.12(d, J=8Hz, 2H), 12.15(br s, 2H), [FT-NMR (400MHz)] | 1632, 1600, 1558, 1420, 1395, 1302, 1098, 911, 887, 835, 820, 797 |
| 3-33 | White fine crystal | B.: 8.00(dd, J=8 and 7Hz, 2H), 8.20(dd, J=8 and 7Hz, 2H), 8.24(d, J=8Hz, 2H), 8.47(d, J=8Hz, 2H), 8.97(s, 2H), 9.72(s, 2H), [FT-NMR (400MHz)] | 1635, 1610, 1578, 1544, 1492, 1381, 1364, 1262, 1239, 1208, 897 |
| 4-1 | White crystal | B.: 3.3–3.9(m, 8H), 7.17(m, 2H), 7.90 (dd, J=8.8, 5.6Hz, 2H), 8.37(ddd, J=8.8, 2.5, 1.4Hz, 2H), 8.48 (bd d, J=5.6Hz, 2H), 9.08(br d, J=2.5Hz, 2H), 10.47(br s, 2H), 10.7–11.5(br, 2H) | 3342, 1707, 1562, 1544, 1527, 1452, 1355, 1233, 878, 807, 761, 727, 676 |
| 4-2 | White crystal hygroscopic | B.: 3.01(s, 6H), 6.81(br t, J=6.5Hz, 2H), 7.08(br d, J=8.2Hz, 2H), 7.70–7.97 (m, 4H), 8.5–10.0(br, 4H) | 1675, 1626, 1578, 1493, 1456, 1405, 1382, 1284, 1236, 1164, 1071, 860, 764, 685 |

The compounds of this invention are expected to serve as an antineoplastic agent as described below. Various known methods can be used for the preparation of medicaments with these compounds and their administration. As the way of administration, injection, peroral administration, rectal application, etc., are possible. As for the form of medicaments, they may take the form of injection, powder, granules, tablet, suppository, etc.

In preparation of medicaments, various types of carriers and adjuvants ordinarily used in pharmaceutical preparations, such as stabilizer, aseptic, anodyne, emulsifier, etc., may be used as occasion demands so long as they give no adverse effect to the selenium compound used as base material.

The content of the selenium compound in a piece of medicament may vary over a wide range according to the form of the medicament and other factors, but usually the selenium compound is contained in a ratio of 0.01 to 100%, preferably 0.1 to 70% (by weight), the rest of the medicament comprising the carrier and other adjuvants.

The recommended dosage per day of the compounds of this invention, as determined from the basic potency experiments, is 0.01 to 10 mg/kg, preferably 0.1 to 2 mg/kg in the case of peroal administration, 0.01 to 5 mg/kg, preferably 0.1 to 1 mg/kg in the case of injection, and 0.01 to 10 mg/kg, preferably 0.1 to 2 mg/kg in the case of suppository.

The antineoplastic and antimutagenic activities of the compounds of this invention, as determined experimentally, are shown below.

Test Example 1

Antineoplastic activity against Enrlich carcinoma

Testing method:
Approximately $10^6$ cells/0.2 ml of Enrlich carcinoma were inoculated into the abdominal cavity of each of the 5-week-old ICR mice (male) used for the test, and the test compounds were administered intraperitoneally to the mice of the treated group once a day for a period of 7 days, starting from the day after said inoculation. The mice of the control group was administered with a saline solution in the same way. Observation of the animals of both groups was continued for 60 days after the administration, and the life prolongation rate (T/C%, T/C×100) was determined from the average duration (days) of life of the mice of the treated group (T) and that of the mice of the control group (C). Also, the 50% lethal dose (LD$_{50}$) was determined from the number of the mice in the treated group which died due to the toxicity of the compound administered.

The results are shown in Table 3.

TABLE 3

| Compound No. | Life prolongation rate (T/C %) | | | | LD$_{50}$ (mg/kg/ day × 7) |
|---|---|---|---|---|---|
| | 2.0* | 4.0* | 8.0* | 16.0* | |

TABLE 3-continued

| Compound No. | 1.0* | 2.0* | 4.0* | 8.0* | 16.0* | LD$_{50}$ (mg/kg/day × 7) |
|---|---|---|---|---|---|---|
| 1-1 | 165 | 173 | 181 | 130 Note 1) | | 8–16 |
| 1-2 | 176 | 169 | 194 | 75 | | 8–16 |
| 1-3 | 200 | 222 | 180 | 83 | | 8–16 |
| 1-4 | 208 | 232 | 168 | 108 | | 8–16 |
| 1-5 | 207 | 174 | 249 | 59 (Note 1) | | 8–16 |
| 1-6 | 173 | 209 | 244 | 103 (Note 1) | | 8–16 |
| 1-7 | 175 | 222 | 256 | 201 (Note 1) | | 8–16 |
| 1-8 | 183 | 220 | 171 | 157 (Note 1) | | 8–16 |
| 1-9 | 171 | 204 | 229 | 228 | | >16 |
| 1-10 | 251 | 192 | 203 | 199 | | >16 |
| 1-11 | 166 | 180 | 230 | 221 | | >16 |
| 1-12 | 194 | 219 | 201 | 140 (Note 2) | | 8–16 |
| 1-13 | 142 | 172 | 158 | 84 (Note 1) | | 8–16 |
| 1-14 | 163 | 179 | 202 | 147 (Note 1) | | 8–16 |
| 1-15 | 154 | 174 | 191 | 162 (Note 1) | | 8–16 |
| 1-22 | 214 | 208 | 233 | 118 (Note 3) | | 8–16 |
| 1-23 | 219 | 181 | 203 | 226 (Note 2) | | 8–16 |
| 1-24 | 168 | 185 | 199 | 181 | | >16 |
| 1-25 | 163 | 141 | 179 | 149 | | >16 |
| 1-26 | 119 | 227 | 153 | 106 (Note 1) | | 8–16 |
| 1-27 | 168 | 234 | 224 | 88 (Note 3) | | 8–16 |
| 1-28 | 138 | 217 | 215 | 264 (Note 1) | | >16 |
| 1-29 | 147 | 205 | 164 | 106 (Note 1) | | 8–16 |
| 1-30 | 258 | 220 | 219 | 198 | | >16 |
| 1-31 | 192 | 182 | 281 | 189 | | >16 |
| 1-32 | 168 | 176 | 208 | 195 | | >16 |
| 1-33 | 138 | 213 | 214 | 205 | | >16 |
| 1-34 | 122 | 159 | 187 | 190 | | >16 |
| 1-35 | 135 | 195 | 225 | 149 | | 8–16 |
| 1-36 | 155 | 186 | 225 | 197 | | >16 |
| 1-37 | 106 | 123 | 214 | 127 | | >16 |
| 1-38 | 181 | 180 | 160 | 126 (Note 1) | | 8–16 |
| 1-39 | 191 | 227 | 240 | 135 | | 16 |
| 1-40 | 214 | 230 | 243 | 123 (Note 2) | | 8–16 |
| 1-41 | 230 | 237 | 312 | 60 | | 8–16 |
| 1-42 | 163 | 176 | 206 | 151 (Note 4) | | 8–16 |
| 1-43 | 247 | 220 | 238 | 52 (Note 3) | | 8–16 |
| 1-44 | 183 | 268 | 253 | 123 (Note 1) | | 8–16 |
| 1-45 | 184 | 170 | 203 | 84 (Note 1) | | 8–16 |
| 1-46 | 229 | 248 | 188 | 59 (Note 3) | | 8–16 |
| 1-47 | 238 | 241 | 241 | 24 (Note 3) | | 8–16 |
| 1-17 | 208 | 212 | 339 | 166 (Note 1) | | 8–16 |
| 2-1 | 185 | 171 | 222 | 146 | | >16 |
| 2-2 | 142** | 199** | 193** | 95** | | 8–16 |
| 2-4 | 152** | 227** | 235** | 173** | | >16 |
| 2-5 | 142** | 214** | 247** | 159** | | >16 |
| 2-6 | 138** | 163** | 233** | 97** | | 16 |
| 2-7 | 201** | 243** | 214** | 67** | | 8–16 |
| 2-8 | 199** | 187** | 191** | 138** | | 8–16 |
| 2-9 | 214 | 221 | 224 | 151 | | >16 |
| 2-10 | 169 | 215 | 175 | 175 | | >16 |
| 2-11 | 112 | 132 | 186 | 218 | | >16 |
| 2-12 | 122 | 123 | 140 | 187 | | >16 |
| 2-13 | 152 | 180 | 185 | 97 (Note 5) | | >16 |
| 2-14 | 158 | 127 | 187 | 165 | | >16 |
| 3-1 | — | 177 | 179 | 193 | 90 | 8–16 |
| 3-2 | — | 178 | 232 | 207 | 63 (Note 2) | 8–16 |
| 3-3 | 172 | 205 | 230 | 212 | — | >8 |
| 3-4 | — | 156 | 208 | 180 | 53 (Note 1) | 8–16 |
| 3-5 | — | 154 | 194 | 223 | 167 (Note 1) | >16 |
| 3-6 | — | 210 | 216 | 253 | 95 (Note 3) | 8–16 |
| 3-7 | — | 143 | 148 | 201 | 119 (Note 1) | 8–16 |
| 3-8 | 208 | 250 | 194 | 212 | — | >8 |
| 3-9 | — | 152 | 204 | 223 | 194 | >16 |
| 3-10 | — | 192 | 238 | 229 | 109 | 8–16 |
| 3-11 | — | 160 | 252 | 279 | 240 | >16 |
| 3-12 | — | 169 | 183 | 232 | 190 | >16 |
| 3-13 | — | 138 | 160 | 171 | 165 | >16 |
| 3-14 | — | 130 | 170 | 243 | 242 | >16 |
| 3-15 | — | 111 | 153 | 192 | 214 | >16 |

*Dose (mg/kg/day),
**Solvent used: DMSO
(Note 1) Administered for 4 days.
(Note 2) Administered for 2 days.
(Note 3) Administered for 3 days.
(Note 4) Administered for 5 days.
(Note 5) Administered for 6 days.

Test Example 2

Antimutagenic activity

Testing method:

The antimutagenic activity was examined according to the Ames method by using Salmonella typhimurium TA-98 as test bacterium and Benzo($\alpha$)pyrene (B($\alpha$)P) as (TA-98) mutagen.

To a solution of 5 μg of B($\alpha$)P and a proper amount of a compound of this invention in 0.1 ml of DMSO were added 0.5 ml of S-9 mix and 0.1 ml of a TA-98 suspension, and the mixture was subjected to preincubation at 37° C. for 20 minutes.

This preincubated mixture was further added with 2 ml of soft agar, and after sufficient mixing, the mixture was uniformly spread on a gluclose minimum agar medium plate and incubated at 37° C. for 48 hours. Thereafter, the number of the colonies produced by reverse mutation was counted.

The number of the colonies existing in the medium containing neither B($\alpha$)P nor the compound of this invention was given as background.

The antimutagenic activity was determined as a mutation inhibition rate from the following formula:

$$\text{Inhibition rate (\%)} = \left[1 - \left\{\frac{\text{number of colonies formed when compound of this invention was added} - \text{background}}{\text{number of colonies formed when no compound of this invention was added} - \text{background}}\right\}\right] \times 100$$

The results are shown in Table 4.

TABLE 4

Inhibitory activity of the compound of this invention against mutagenic action of benzpyrene

| Compound | | Background | Amount of compound used (μg/plate) | | | | | | | |
|---|---|---|---|---|---|---|---|---|---|---|
| | | | 0 | 0.5 | 1 | 5 | 10 | 50 | 100 | 500 |
| 1-41 | Number of colonies (Inhibition rate) | 33 — | 298 (0) | 238 (22.6) | 234 (24.2) | 209 (33.6) | 149 (56.2) | 119 (67.5) | 96 (76.2) | 16 (100) |

The compounds of this invention have a high antineoplastic activity against the malignant tumors such as ascitic cancer, liver cancer, etc. They also have an antimutagenic activity, and their effective use as an antineoplastic agent is expected.

The preparation process of the compounds of this invention will be described concretely below by showing the examples thereof.

EXAMPLE 1-1

Synthesis of Compound No. 1-22

386 mg (1.52 mmol) of a selenium oxychloride-1,4-dioxane complex was weighted and dissolved in 4 ml of anhydrous methylene chloride. To this solution was added dropwise at room temperature 4.2 ml of a solution prepared by diluting 250 mg (3.04 mmol) of N-methylimidazole with anhydrous methylene chloride. The resulting pale-yellow solution was allowed to stand for about 30 minutes and then concentrated and evaporated to dryness under reduced pressure to obtain 503 mg of yellow fine crystals (yield: 100.0%).

Compound No.s 1-2 to 1-31, 1-33 to 1-39, 1-51 and 1-52 were synthesized in the same way as described above by using the corresponding compounds in place of N-methylimidazole.

Also, compound Nos. 1-1 and 1-32 were synthesized by using a selenium oxybromide-1,4-dioxane (1:1) complex in place of the selenium oxychloride-1,4-dioxane (1:1) complex and by reacting it with the corresponding compounds.

The properties of these compounds are shown in Table 2.

EXAMPLE 1-2

Synthesize of compound No. 1-41

419 mg (1.65 mmol) of a selenium oxychloride-1,4-dioxane (1:1) complex was dissolved in 2 ml of anhydrous methylene chloride. To this solution, 2 ml of an anhydrous methylene chloride solution of 258 mg (1.65 mmol) of 2,2'-dipyridyl was added dropwise gradually under shaking at room temperature. After the dropwise addition, the mixture was left standing for one hour. Thereafter, the supernatant was removed, leaving the produced fine crystal powder. The reside was washed with a small quantity of anhydrous methylene chloride and then dried in vacuo to obtain 508 mg of slightly yellowish white fine crystal powder (yield: 95.6%).

Compound Nos. 1-40 and 1-43 to 1-45 were synthesized in the similar way by using the corresponding compounds in place of 2,2'-dipyridyl.

Compound No. 1-42 was synthesized by using a selenium oxybromide-dioxane (1:1) complex as starting material and reacting it with 2,2'-dipyridyl.

The properties of these compounds are shown in Table 2.

EXAMPLE 1-3

Synthesis of compound No. 1-47

310 mg (1.22 mmol) of selenium oxychloride-1,4-dioxane (1:1) complex was dissolved in 3 ml of anhydrous methylene chloride, and to this solution was added dropwise a 1.6 ml of anhydrous methylene chloride solution of 193 mg (2.44 mmol) of anhydrous pyridine under shaking at room temperature. 15 minutes thereafter, a 1 ml of anhydrous methylene chloride solution of 118 mg (2.56 mmol) of anhydrous ethyl alcohol was further added dropwise thereto under shaking. After the dropwise addition ended, the mixture was left standing for 30 minutes and then the solvent was removed gradually under reduced pressure to obtain 453 mg of white wet powder (yield: 100.3%).

Compound Nos. 1-46 and 1-48 to 1-50 were synthesized by the same reaction procedure as above but using the corresponding alcohols in place of ethanol.

The properties of these compounds are shown in Table 2.

EXAMPLE 2-1

Synthesis of compound No. 2-13 (C4SDp)

250 mg (1.23 mmol) of tetrachloroselenium was weighed and dissolved in 10 ml of anhydrous tetrahydrofuran. To the resulting light-yellow solution was added dropwise 3.8 ml of an anhydrous tetrahydrofuran solution of 177 mg (1.13 mmol) of 2,2'-dipyridyl under ice-water cooling. Thereafter, the mixture was left standing under ice-water cooling for one hour. After the end of the reaction, the supernatant was removed, leaving the produced yellow crystal powder. The residue was washed with a small quantity of anhydrous tetrahydrofuran and then dried in vacuo to obtain 380 mg of yellow fine crystal powder (yield: 89.1%).

EXAMPLE 2-2

Synthesis of compound No. 2-5 (C4S4Ph)

255 mg (1.16 mmol) of tetrachloroselenium was weighed and dissolved in 4 ml of anhydrous tetrahydrofuran to form a light-yellow solution. To this solution was added dropwise 4.6 ml of an anhydrous tetrahydrofuran solution of 358 mg (2.31 mmol) of 4-phenylpyridine at room temperature. Thereafter, the mixture was allowed to stand at room temperature for 2 hour. After the end of the reaction, the reaction mixture was concentrated and evaporated to dryness under reduced pressure to obtain 615 mg of yellow fine crystal powder (yield: 100.2%).

Compound Nos. 2-1 to 2-12 were synthesized by the similar reaction procedure as above.

EXAMPLE 2-3

Synthesis of compound No. 2-14 (B4SDp)

448 mg (1.12 mmol) of tetrabromoselenium was weighed and dissolved in 10 ml of anhydrous diethyl ether. To this solution was added dropwise 5 ml of an anhydrous diethyl ether solution of 175 mg (1.12 mmol) of 2,2'-dipyridyl at room temperature. Thereafter, the mixture was allowed to stand at room temperature for 2 hours. After the end of the reaction, the supernatant was removed, leaving the produced light-brown powder. The latter was washed with a small quantity of anhydrous diethyl ether and then dried in vacuo to obtain 574 mg of light-brown powder (yield: 92.1%).

EXAMPLE 3-1

Synthesis of compound No. 3-6 (SOCH)

370 mg (1.457 mmol) of selenium oxychloride-1,4-dioxane (1:1) complex was dissolved in 11 ml of anhydrous methylene chloride, and to this solution was slowly added dropwise a 3 ml of anhydrous methylene chloride solution of 286 mg (2.91 mmol) of cyclohexene oxide under shaking at room temperature. 3 hours thereafter, the mixed solution was concentrated under reduced pressure and then the solvent was removed completely to obtain 513 mg of a slightly yellowish viscous oil of bis-(2-chlorocyclohexyl)selenite (SOCH) (yield: 97.2%).

In the same way, compound Nos. 3-1 to 3-7 were synthesized by using the corresponding oxides shown below.

| Oxide | Obtained compound No. |
|---|---|
| 2,3-epoxybutane | 3-1 |
| 2-methyl-1,2-epoxypropane | 3-2 |
| 1,2-epoxybutane | 3-3 |
| 1,2-epoxyoctane | 3-4 |
| Styrene oxide | 3-5 |
| 2,3-epoxynorbornane | 3-7 |

EXAMPLE 3-2

Synthesis of compound No. 3-8 (SOEEC)

3.33 g (0.0131 mmol) of selenium oxychloride-1,4-dioxane (1:1) complex was dissolved in 33 ml of anhydrous 1,4-dioxane, and to this solution was added 2.83 g (0.0288 mol) of anhydrous potassium acetate, followed by stirring at room temperature. 24 hours later, 1.125 g (0.0125 mol) of 1,2-butanediol was added and the mixture was further stirred for 2 days. Thereafter, the mixed solution was subjected to suction filtration and the byproduced potassium chloride was removed. The solution portion was concentrated and then distilled under reduced pressure to obtain 1.657 g of 1,2-butanediolselenite (SOEEC) as a colorless oil having a boiling point of 110.5°–112.0° C. (6 mmHg) (yield: 72.5%).

EXAMPLE 3-3

Synthesis of compound No. 3-9 (SOEPC)

828 mg (4.99 mmol) of selenium oxychloride was dissolved in 25 ml of anhydrous diethyl ether, and to this solution was added 1,078 mg (10.98 mmol) of anhydrous potassium acetate and stirred at room temperature. 20 hours, later, 660 mg (4.99 mmol) of 2,2-diethyl-1,3-propanediol was added and the mixture was further stirred for 24 hours. Thereafter, the mixture was subjected to suction filtration and the byproduced potassium chloride was removed. The resulting transparent solution was concentrated under reduced pressure and then the solvent was removed perfectly to obtain 1,019 mg of 2,2-diethyl-1,3-propanediol as a slightly yellowish viscous oil (yield: 90.7%).

EXAMPLE 3-4

Synthesis of compound No. 3-14 (SC4Hy.aq)

1.6 ml of methanol containing 1.5–2% of water and 16 ml of methylene chloride were added to 306 mg (3.22 mmol) of 4-hydroxypyridine and the latter was dissolved. To this solution was added dropwise a 4 ml anhydrous methylene chloride solution of 409 mg (1.61 mmol) of selenium oxychloride-1,4-dioxane complex under shaking over a period of 6 minutes. 2 Hours thereafter, the resulting transparent solution was concentrated under reduced pressure to obtain 633 mg of white fine crystals (yield: 107.8%). This product was washed several times with a small quantity of anhydrous methylene chloride and dried in vacuo to obtain 428 mg of a selenium oxychloride-4-hydroxypyridine (1:2) complex mono hydrate as white fine crystals (yield: 72.9%).

Compound Nos. 3-11, 3-28, 4-1 and 4-2 were synthesized in the same way as described above by using the following compounds of A in the formula (I) in place of 4-hydroxypyridine.

| Starting compound (A in the formula (I)) | Obtained compound No. |
|---|---|
| 4-aminopyridine | 3-11 |
| 2-aminopyridine | 3-28 |
| N—(2-chloroethyl)-N'—(3-pyridyl)urea | 4-1 |
| 2-(N—methylamino)pyridine | 4-2 |

EXAMPLE 3-5

Synthesis of compound No. 3-23 (SC5NI)

396 mg (1.56 mmol) of selenium oxychloride-1,4-dioxane complex was dissolved in 4 ml of anhydrous methylene chloride. To this solution was added dropwise at room temperature 5 ml of an anhydrous methylene chloride solution containing 544 mg (3.12 mmol) of 5-nitroisoquinoline. The resulting light-yellow solution was left standing as it was for about 60 minutes and then concentrated and evaporated to dryness under reduced pressure to obtain 809 mg of yellow fine crystals (yield: 100.6%).

Compound No.s 3-10, 3-12, 3-13, 3-15, 3-18 to 3-22, 3-24 to 3-26, and 3-29 to 3-33 were synthesized by conducting the same operations as described above but by using the following compounds of A in the formula (I) in place of 5-nitroisoquinoline.

| Starting compound (A in the formula (I)) | Obtained compound No. |
|---|---|
| 4-benzoylpyridine | 3-10 |
| 4-dimethylaminopyridine | 3-12 |
| 2-hydroxypyridine | 3-13 |
| 4-methoxypyridine | 3-15 |
| allyl isonicotinate | 3-18 |
| 1,6-naphthylidine | 3-19 |
| 5-nitroquinoline | 3-20 |
| 6-nitroquinoline | 3-21 |
| 8-nitroquinoline | 3-22 |
| Theophylline | 3-24 |
| 2,2'-bi(methyl isonicotinate) | 3-25 |
| 2,2'-bi(ethyl isonicotinate) | 3-26 |
| 6-aminonicotinamide | 3-29 |
| 2-hydroxy-5-nitropyridine | 3-20 |
| 4-hydroxyquinoline | 3-31 |
| 8-hydroxyquinoline | 3-32 |
| 4-bromoisoquinoline | 3-33 |

What is claimed is:

1. A selenium compound represented by the general formula (I):

$$SeOCl_2(A)_n(Y)_m \qquad (I)$$

wherein n is 1 or 2, and m is 0 or 1, A is 2,2'-dipyridyl or a group represented by the formula:

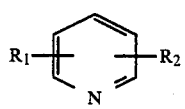

(wherein $R_1$ is hydrogen atom and $R_2$ is a hydroxyl group), and Y is $H_2O$.

2. A selenium compound according to claim 3 which is a selenium oxychloride-2,2'-dipyridyl (1:1) complex.

3. A selenium compound according to claim 1 which is a selenium oxychloride-4-hydroxypyridine (1:2) complex mono hydrate.

* * * * *